US010067101B2

(12) United States Patent
Traudt et al.

(10) Patent No.: US 10,067,101 B2
(45) Date of Patent: Sep. 4, 2018

(54) GAS CHROMATOGRAPHY (GC) COLUMN HEATER

(71) Applicant: Agilent Technologies, Inc., Santa Clara, CA (US)

(72) Inventors: Sammye Elizabeth Traudt, Middletown, DE (US); Richard P White, Glen Mills, PA (US); William H Wilson, Newark, DE (US); Paul C Dryden, Lincoln University, PA (US); Jane Ann Leous, Philadelphia, PA (US)

(73) Assignee: AGILENT TECHNOLOGIES, Santa Clara, CA (US)

( * ) Notice: Subject to any disclaimer, the term of this patent is extended or adjusted under 35 U.S.C. 154(b) by 75 days.

(21) Appl. No.: 14/802,864

(22) Filed: Jul. 17, 2015

(65) Prior Publication Data

US 2016/0077064 A1 Mar. 17, 2016

Related U.S. Application Data

(60) Provisional application No. 62/050,125, filed on Sep. 13, 2014.

(51) Int. Cl.
*G01N 30/90* (2006.01)
*G01N 30/54* (2006.01)
(Continued)

(52) U.S. Cl.
CPC ......... *G01N 30/54* (2013.01); *G01N 30/6095* (2013.01); *G01N 2030/025* (2013.01)

(58) Field of Classification Search
CPC ............. G01N 2030/025; G01N 30/88; G01N 30/6095; G01N 2030/8854; G01N 30/02; G01N 30/30
(Continued)

(56) References Cited

U.S. PATENT DOCUMENTS 3,213,596 A 10/1965 Gill
4,923,486 A * 5/1990 Rubey .................... G01N 30/30
95/87
(Continued)

FOREIGN PATENT DOCUMENTS

CN 2525514 Y 12/2002
CN 202994749 U 6/2013
(Continued)

OTHER PUBLICATIONS

Wang, A., et al., "Gas Chromatography Using Resistive Heating Technology," Journal of Chromatography A, 2012, vol. 1261, pp. 46-57.
(Continued)

*Primary Examiner* — Eric S McCall
*Assistant Examiner* — Mohammed E Keramet-Amircola

(57) ABSTRACT

A gas chromatography (GC) column heating apparatus is described. The GC column heating apparatus includes a first substrate; a heating element disposed over the first substrate; and a second substrate. A gas chromatography (GC) column heating and cooling apparatus is also described. The GC column cooling and heating apparatus includes a housing configured to receive a heating apparatus, the heating apparatus comprising a first side and a second side; a first thermal insulation layer disposed over the first side; a second thermal insulation layer disposed over the second side; and an actuator connected to the housing and configured to move the first and second thermal insulation layers in contact with the first and second sides, respectively, during a heating sequence, and to move the first and second layers of insulation out of contact with the first and second sides, respectively, during a cooling sequence.

21 Claims, 9 Drawing Sheets

(51) Int. Cl.
*G01N 30/60* (2006.01)
*G01N 30/02* (2006.01)

(58) Field of Classification Search
USPC .................................. 73/23.39, 23.35, 23.22
See application file for complete search history.

(56) References Cited

U.S. PATENT DOCUMENTS

| | | | | |
|---|---|---|---|---|
| 5,782,964 | A * | 7/1998 | Mustacich | G01N 30/30 73/23.25 |
| 5,808,178 | A * | 9/1998 | Rounbehler | G01N 30/30 73/23.35 |
| 5,856,616 | A * | 1/1999 | Maswadeh | G01N 30/16 422/89 |
| 5,939,614 | A * | 8/1999 | Walters | G01N 30/30 422/88 |
| 6,029,498 | A | 2/2000 | Walters et al. | |
| 6,068,604 | A * | 5/2000 | Krause | G01N 3/405 600/587 |
| 6,171,378 | B1 | 1/2001 | Manginell et al. | |
| 6,454,840 | B1 * | 9/2002 | Gellert | G01N 30/6095 55/DIG. 5 |
| 6,607,580 | B1 * | 8/2003 | Hastings | G01N 30/30 95/87 |
| 6,666,907 | B1 * | 12/2003 | Manginell | G01N 30/6095 73/23.36 |
| 6,966,212 | B2 * | 11/2005 | Klee | G01N 30/12 73/23.41 |
| 7,396,468 | B2 * | 7/2008 | Boyes | C07K 1/18 210/198.2 |
| 7,513,936 | B2 | 4/2009 | Rogues | |
| 9,194,849 | B2 | 11/2015 | Kanai et al. | |
| 2003/0228452 | A1 | 12/2003 | Yu | |
| 2004/0139785 | A1 * | 7/2004 | Abdul-Khalek | F02D 41/1467 73/28.01 |
| 2005/0184054 | A1 * | 8/2005 | Kachi | H01L 21/67103 219/546 |
| 2006/0283324 | A1 * | 12/2006 | Roques | G01N 30/6095 96/101 |
| 2007/0266858 | A1 * | 11/2007 | Alm | G01N 30/463 96/105 |
| 2009/0272270 | A1 * | 11/2009 | McGill | B01J 20/205 96/101 |
| 2010/0043527 | A1 * | 2/2010 | Marra | B60H 1/008 73/28.02 |
| 2010/0044288 | A1 | 2/2010 | Kitagawa | |
| 2010/0243635 | A1 * | 9/2010 | Nakamura | F23Q 7/22 219/270 |
| 2011/0265551 | A1 * | 11/2011 | Hopka | G01N 27/4067 73/23.31 |
| 2012/0160038 | A1 * | 6/2012 | Wells | B01J 15/00 73/863.21 |
| 2013/0043380 | A1 * | 2/2013 | Correale | G01N 1/2202 250/252.1 |
| 2014/0119993 | A1 * | 5/2014 | Rhodes | G01N 21/766 422/52 |

FOREIGN PATENT DOCUMENTS

| | | |
|---|---|---|
| JP | 61288154 A | 12/1986 |
| JP | 05036363 U | 5/1993 |
| JP | 08145972 A | 6/1996 |

OTHER PUBLICATIONS

International Search Report and Written Opinion for PCT/US2015/040999 dated Oct. 16, 2015.
PCT International Search Report and the Written Opinion of the International Searching Authority regarding PCT/US2015/041004 dated Oct. 19, 2015.
EPO, et al., Extended European Search Report & Written Opinion dated Jan. 30, 2018, Application No. 15840430.1, 9 Pages.

* cited by examiner

GAS CHROMATOGRAPHY (GC) COLUMN HEATER

CROSS-REFERENCE TO RELATED APPLICATIONS

The present application claims priority under 35 U.S.C. § 119(e) from U.S. Provisional Application No. 62/050,125 filed on Sep. 13, 2014, naming Sammye Traudt, et al. as inventors. The entire disclosure of U.S. Patent Application No. 62/050,125 is specifically incorporated herein by reference.

BACKGROUND

In GC systems, the amount of time required for a chemical compound to traverse the entire length of a separation column ("column") is known as its retention time. One factor that contributes to the retention time of a chemical compound is the temperature of the separation column. Controlling the temperature of the column precisely from analysis to analysis is beneficial to provide repeatability in the retention time for a particular chemical compound, or analyte. In addition, programmatically changing the column temperature while the sample analytes are migrating through it can advantageously provide shorter analysis time and reduce peak broadening.

Often, columns are heated in known systems using an air convection oven because of its ability to provide a uniform and repeatable thermal environment in a space large enough to accommodate a wide variety of column diameters and lengths. The columns are typically arranged on a support structure that creates an open cylinder. This allows the heated air access over all the column surfaces and results in uniform temperatures across the entire column length. While air convection ovens are useful, their use comes with clear disadvantages. For example, convection ovens require a significant amount of energy and time to heat up, and a significant amount of time to cool down. This leads, of course, to comparatively long cycle times and high power consumption, among other disadvantages. In addition, the ability to do rapid analysis via temperature programmed conditions is limited when using air convection ovens.

What is needed, therefore, is an apparatus that overcomes at least the drawbacks of known GC column heaters discussed above.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DEFINED TERMINOLOGY

Figure 1:
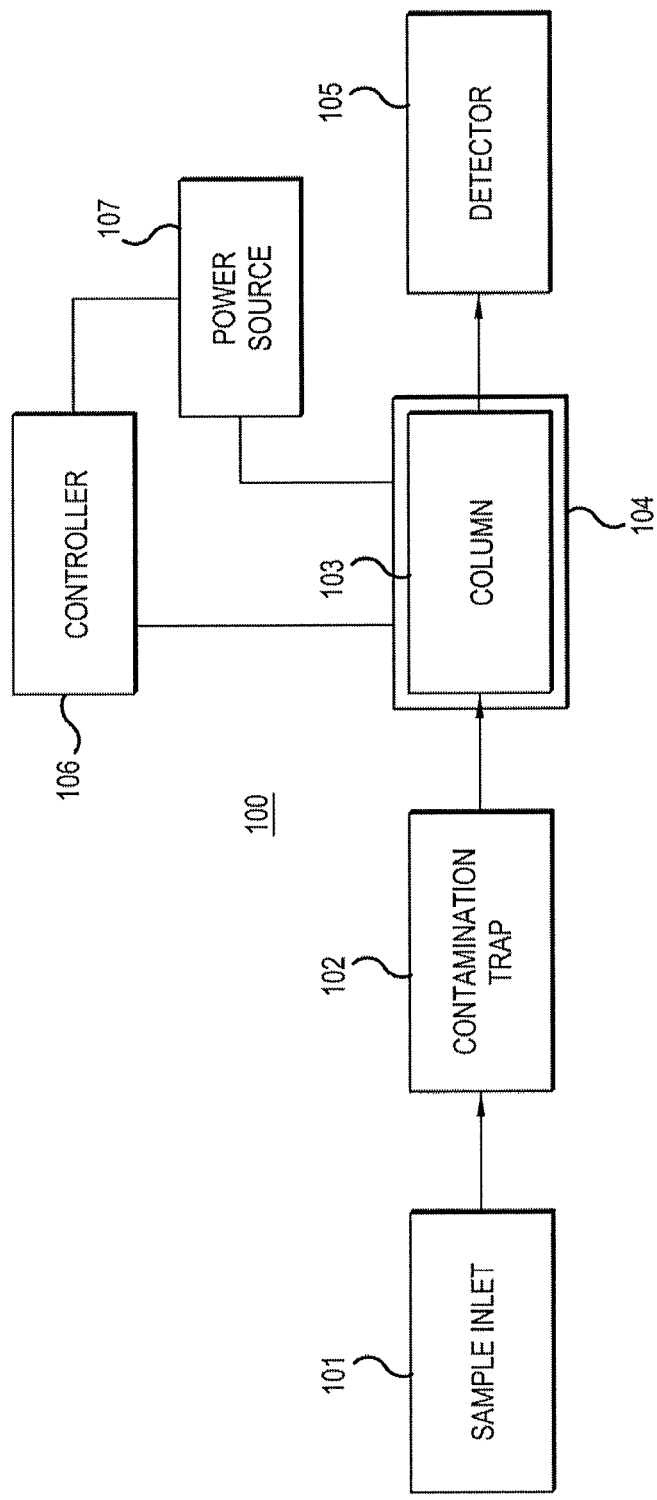
FIG. 1 is a simplified block diagram of a GC system in accordance with a representative embodiment.

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms 'a', 'an' and 'the' include both singular and plural referents, unless the context clearly dictates otherwise. Thus, for example, 'a device' includes one device and plural devices.

As used in the specification and appended claims, and in addition to their ordinary meanings, the terms 'substantial' or 'substantially' mean to within acceptable limits or degree. For example, 'substantially cancelled' means that one skilled in the art would consider the cancellation to be acceptable.

As used in the specification and the appended claims and in addition to its ordinary meaning, the term 'approximately' means to within an acceptable limit or amount to one having ordinary skill in the art. For example, 'approximately the same' means that one of ordinary skill in the art would consider the items being compared to be the same.

DETAILED DESCRIPTION

In the following detailed description, for purposes of explanation and not limitation, representative embodiments disclosing specific details are set forth in order to provide a thorough understanding of the present teachings. Descriptions of known systems, devices, materials, methods of operation and methods of manufacture may be omitted so as to avoid obscuring the description of the example embodiments. Nonetheless, systems, devices, materials and methods that are within the purview of one of ordinary skill in the art may be used in accordance with the representative embodiments.

Relative terms, such as "above," "below," "top," "bottom," "upper" and "lower" may be used to describe the various elements' relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be "below" that element. Similarly, if the device were rotated by 90° with respect to the view in the drawings, an element described "above" or "below" another element would now be "adjacent" to the other element; where "adjacent" means either abutting the other element, or having one or more layers, materials, structures, etc., between the elements. As used herein, an element "disposed over" or "disposed below" another element means the element is "adjacent to" the other element. "Directly adjacent" means abutting the other element.

FIG. 1 is a simplified block diagram of a GC system 100 in accordance with a representative embodiment. Many aspects of the GC system 100 are known to one of ordinary skill in the art. As such, details of certain known components of the GC system 100 are omitted. In certain instances representative examples of known components that may be implemented are noted, but are presented for illustration and are, in no way, intended to be limiting.

The GC system 100 comprises a sample inlet 101. The sample inlet 101 is fluidically coupled to a contaminant trap 102. The contaminant trap 102 is fluidically coupled to a column 103, which may be one of a variety of columns useful in gas chromatography. In an embodiment, the contaminant trap 102 may be as described in concurrently filed, commonly owned U.S. patent application Ser. No. 14/057,022 (filed Oct. 18, 2013), the disclosure of which is specifically incorporated herein by reference. The contaminant trap 102 is a microfluidic contaminant trap configured to trap contaminants in the sample from the sample inlet 101 and to prevent the trapped contaminants from reaching the column 103. It is noted that the inclusion of contaminant trap 102 is merely illustrative, and the present teachings are contemplated for use in GC systems that do not comprise a contaminant trap, or that do not comprise a microfluidic contaminant trap as described in the application referenced immediately above.

The column 103 separates the components of a chemical sample. The column 103 may be a capillary column comprising a piece of fused silica or metal tubing (not shown) with a coating on the inner portions of the tubing or packed with particles that interact with the sample from sample inlet 101 to separate the components of the chemical sample.

The column 103 is in thermal contact with a column heating apparatus, which is an aspect of the column temperature control apparatus 104. By virtue of the column temperature control apparatus 104, the retention time is controlled, while the uniformity of the heating of the column 103 is improved over previous devices. Furthermore, in certain embodiments, the column temperature control apparatus 104 cools the column 103 in an efficient manner, ultimately improving repeatability of the retention time of an analyte and analysis cycle time compared to known GC systems. These and other benefits of the column temperature control apparatus 104 are described more fully below in connection with representative embodiments.

The column 103 is physically and/or fluidly connected to a detector 105, which detects the presence and frequently the quantity of the components separated by the column 103. Generally, the detector 105 is a known GC detector such as a flame ionization detector (FID), a mass spectrometer detector (MSD), a thermal conductivity detector (TCD), an electron capture detector (ECD), a nitrogen phosphorus detector (NPD), a sulfur chemiluminescence detector (SCD), a nitrogen chemiluminescence detector (NCD), a pulsed flame photometric detector (PFPD), a helium ionization detector (HID), or a flame photometric detector (FPD).

The GC system 100 also comprises a controller 106 and a power source 107. The controller 106 may be one of a plurality of controllers (not shown) of the GC system 100, or may be the sole controller of the GC system. Presently, the function of the controller 106 with respect to maintaining the heating of the column 103 by the column temperature control apparatus 104 is described. Other functions of the controller 106 or of other controllers are not germane to the present teachings and are not described.

Generally, the controller 106 can be implemented in numerous ways (e.g., such as with dedicated hardware) to perform various functions discussed herein. A "processor" is one example of a controller, which employs one or more microprocessors that may be programmed using software (e.g., microcode) to perform various functions discussed herein. The controller 106 may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, microcontrollers, application specific integrated circuits (ASICs), and field-programmable gate arrays (FPGAs).

In various implementations, the controller 106 may be associated with one or more storage media (generically referred to herein as "memory," e.g., volatile and non-volatile computer memory such as random-access memory (RAM), read-only memory (ROM), programmable read-only memory (PROM), electrically programmable read-only memory (EPROM), electrically erasable and programmable read only memory (EEPROM), universal serial bus (USB) drive, floppy disks, compact disks, optical disks, magnetic tape, etc.). In some implementations, the storage media may be encoded with one or more programs that, when executed on the controller 106, perform at least some of the functions discussed herein. Various storage media may be fixed within the controller 106 or may be transportable, such that the one or more programs stored thereon can be loaded into a processor or controller so as to implement various aspects of the present teachings discussed herein. The terms "program" or "computer program" are used herein in a generic sense to refer to any type of computer code (e.g., software or microcode) that can be employed to program the controller 106.

The controller 106 is configured to receive temperature data from a temperature sensor (not shown in FIG. 1), to interpret the data from the temperature sensor, and to execute algorithms to alter system aspects to achieve the desired column temperature. These functions may be performed by separate controllers, processors or modules. The controller 106 is configured to provide control signals to the power source 107. The power source 107 is one of a number of known electrical power sources and is configured to adjust the power of the column temperature control apparatus 104 to maintain the temperature of the column 103 at approximately a desired temperature.

Figure 2A:
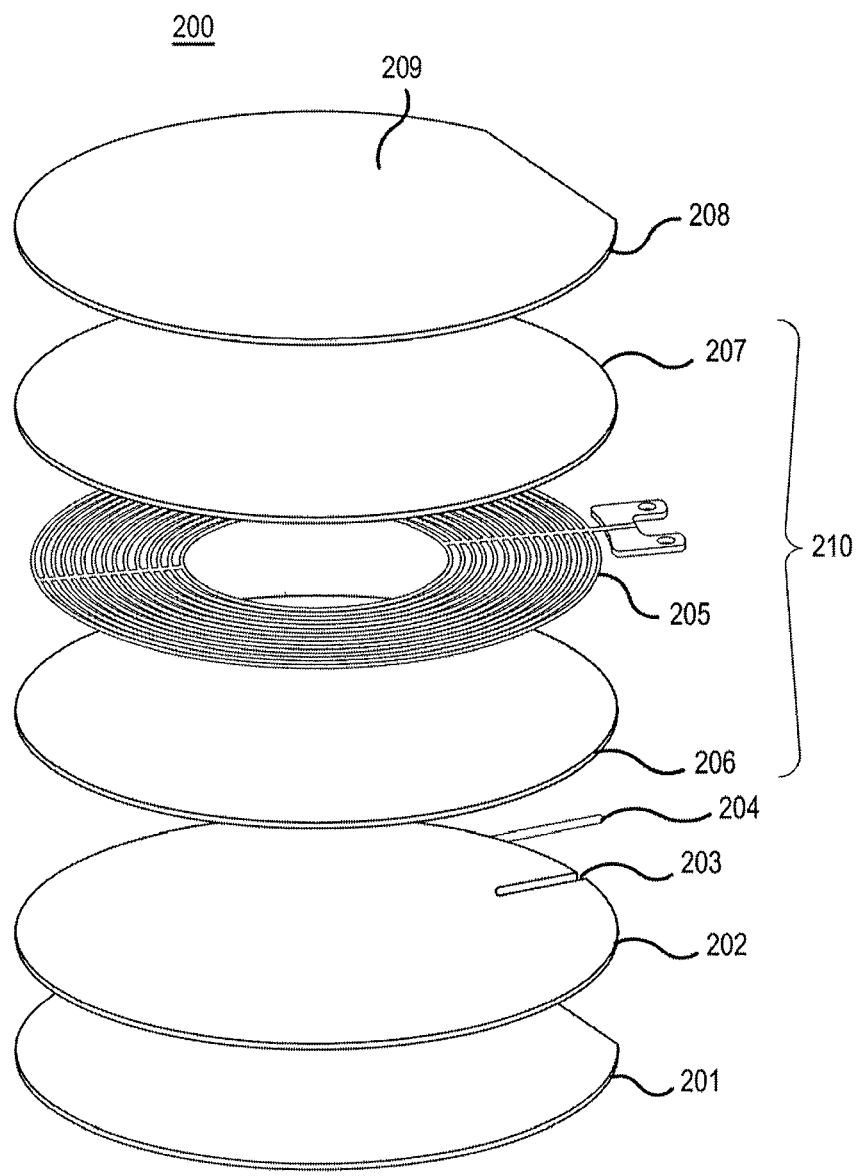
FIG. 2A shows an exploded view of an apparatus for heating a GC column in accordance with a representative embodiment.

FIG. 2A shows an exploded view of a column heating apparatus 200 (sometimes referred to as "an apparatus") for heating a GC column (not shown in FIG. 2A) in accordance with a representative embodiment. The column heating apparatus 200 comprises a first substrate 201, which is substantially planar. A spacer layer 202 is optionally disposed over the first substrate 201. A recess 203 is provided in the layer 202, and is configured to receive a temperature sensor 204.

The heater assembly 210 is disposed over the first substrate 201 and comprises a heating element 205 disposed between an optional first intervening layer 206 and an optional second intervening layer 207. The first and second intervening layers 206, 207 are generally mechanically compliant and made from the same material. Notably, the heater assembly 210 is contemplated for use as the heat source in the column temperature control apparatus 104 described above in connection with the representative embodiments of FIG. 1.

While the heating element 205 is shown as a substantially uniform series of traces, it is also contemplated that that the traces may be substantially non-uniform, non-symmetrical, and/or irregular. By way of example, since the outer edge of the heater assembly 210 is more exposed to the external environment, a decrease in temperature may occur at the outer edge compared to the inner portions of the assembly. By increasing density and/or changing width of the traces of the heating element 205 at its edge, the power density of the heating element 205 near the outer edge is increased, and the temperature differential between the inner portion and the outer edge of the heating element, manifest in the noted temperature decrease, may be reduced or eliminated. Further modifications of the thickness of the traces may also have desirable properties as described herein.

First and second intervening layers 206, 207 may also be selected to act as electrical insulators between the heating element 205 and the first substrate 201 and a second substrate 208, which is disposed over the heater assembly 210. Like the first substrate 201, the second substrate is substantially planar. The second substrate 208 is configured to have the GC column (not shown in FIG. 2A) in direct contact therewith or indirect contact therewith (i.e., with an intervening layer (not shown)) between the GC column and the second substrate 208. Illustratively, the GC column is disposed over an upper surface 209 of the second substrate 208, and heat from the heater assembly 210 is transferred through the second substrate 208 to the GC column. As can be appreciated from a review of FIG. 2A, the upper surface 209 is substantially planar.

The first and second substrates 201, 208 may comprise a single layer or multiple layers of the same or different materials. As described more fully below, the column heating apparatus 200 substantially uniformly heats the GC column contacting the second substrate 208.

In known GC heaters, such as air convection ovens, the oven may require large amounts of power (up to 2000 W) to allow temperature programming rates of 30-60° C./min. By contrast, as described more fully below, the column heating apparatus 200 beneficially provides similar temperature programming rates at substantially less than 100 W. In addition, the column heating apparatus 200 allows much faster temperature programming rates (e.g., up to five to ten times faster than a known GC heater with 25% of the power requirement of the known GC heater), resulting in faster chromatographic analyses. Also, where known GC heaters may take six or more minutes to cool from 450° C. to 50° C., the column heating apparatus 200 can be operated to take less than three minutes, which allows for faster cycle times between analyses. The column heating apparatus 200 realizes these improvements in performance by specifying the material properties of the second substrate 208 or the first and second substrates 201, 208 to be low thermal mass while maintaining mechanical stiffness, small thermal gradients, and resistance to thermal deformation.

As should be appreciated by one of ordinary skill in the art, the "thermal mass" of an object is a measure of its capacity to store thermal energy (i.e., heat). As such, a material that has a comparatively low thermal mass will require less heat in order to change temperature than one of comparatively high thermal mass. As described more fully below, in order to enable faster heating and cooling, the materials selected for the first and second substrates 201, 208 and the heater assembly 210 have a low thermal mass.

Thermal mass (with units of J/K) is the product of the specific heat of the material, $c_p$, and the mass of the object, m. For convenience, mass can be further specified as the product of the density, $\rho$, of the material, a surface area, $A_s$, and a thickness, t, normal to the surface area. Combining, thermal mass can be expressed as:

$$\text{thermal mass} = (\rho c_p t A_s)$$

Since the surface area of the column heating apparatus 200 is fixed based on the size of the column to be heated, the surface area is viewed as a constant for this discussion. The remaining terms are examined further. The term, $\rho c_p$, is also known as the volumetric heat capacity of the material and is an intrinsic property of the material. To minimize thermal mass, this term should be minimized. According to a representative embodiments, materials for the second substrate 208 or the first and second substrates 201, 208 have a volumetric heat capacity less than approximately $$3.0 \times 10^6 \frac{J}{m^3 K} \text{ at } 25° \text{ C.}$$

The selection of material for the second substrate 208 or the first and second substrates 201, 208 is additionally guided by mechanical stiffness, low thermal gradients, and resistance to thermal deformation. These factors are particularly important in determining the minimum thickness of material required for the second substrate 208 or the first and second substrates 201, 208. Along with thermal mass, these are not wholly independent characteristics, so choice of materials is made considering their interrelationship. The ultimate goal is to achieve low thermal gradients across the upper surface 209 of second substrate 208 while achieving a relatively low thermal mass for first and second substrates 201 and 208 to enable faster heating and cooling.

Thermal gradients across the second substrate 208 or across the first and second substrates 201, 208 result from different parts of the substrates being in different thermal environments. The heating element 205, for instance, does not have a completely homogenous thermal profile. In addition, the outer edges of the first and second substrates 201, 208 will typically have more exposure to the ambient temperature environment. As such, thermal gradients can exist across the first and second substrates 201, 208. Gradients are reduced when the material chosen for the first and second substrates has low resistance to heat flow, that is, a high thermal conductivity, k. It is desirable, therefore, to have a material with comparatively high thermal conductivity, particularly for the second substrate 208, so that the upper surface 209 that touches the GC column is substantially uniform in temperature. According to a representative embodiment, materials for the second substrate 208 or the first and second substrates 201, 208 have a thermal conductivity greater than approximately $$100 \frac{W}{mK} \text{ at } 25° \text{ C.}$$

The first and second substrates, 201 and 208, provide mechanical structure for the column heating apparatus 200. Notably, the first and second substrates 201, 208 support the relatively non-rigid heater assembly 210 as well as the layer 202 and the temperature sensor 204. Beneficially, materials chosen for the first and second substrates 201, 208 are sufficiently stiff to provide adequate support. The stiffness of a material is related to its elastic modulus (or Young's Modulus), E. If a material has a high elastic modulus, then less of it (e.g., a thinner piece of it) is necessary to provide the same stiffness as a material with a lower elastic modulus. It is beneficial, therefore, to have a material with a high elastic modulus so that less (thermal) mass of material is required to achieve adequate stiffness. According to a representative embodiment, materials for the first and second substrates 201, 208 have a Young's Modulus greater than approximately 100 GPa. In addition to stiffness, the first and second substrates, 201 and 208 must maintain surface flatness in order to hold the heater and column in direct contact with the upper surface 209, or in indirect contact with the upper surface 209 (i.e., with an intervening layer (not shown) between the GC column 212 and the upper surface 209). Issues in flatness may occur due to deformation or "buckling" from rapid temperature changes. If large thermal gradients exist in a component such as, for example, when the component is cooled asymmetrically, sections of the component will want to grow due to thermal expansion while other sections will want to remain fixed. In the worst case, this can cause buckling or fracture.

The likelihood of mechanical deformation due to thermal expansion can be minimized by choosing a material with a high thermal conductivity, k, low thermal expansion coefficient, α, or both. A material with high thermal conductivity resists the formation of large thermal gradients within the material. Materials with low thermal expansion do not grow very much even under significant thermal gradients. Choosing materials with a high thermal conductivity, low thermal expansion coefficient, or both, allows for the use of less material (e.g., a thinner piece of it) and therefore less thermal mass while providing adequate resistance to buckling. According to a representative embodiment, materials for the second substrate 208 or the first and second substrates 201, 208 have a ratio of thermal conductivity to coefficient of thermal expansion greater than approximately $$25 \frac{W}{m(ppm)} \text{ at } 25°C.$$

Another consideration in the selection of the material for the second substrate 208, or the first and second substrates 201, 208 is the electrical insulating properties of the material. Beneficially, the material is substantially electrically insulating to avoid having to add an additional material in the column heating apparatus 200 to perform this function.

Finally, it is important to select a material for the second substrate 208, or the first and second substrates 201, 208 that is operative in the column heating apparatus 200 at temperatures greater than approximately 450° C.

The table below presents a summary of some of the factors to be considered in selection of the material for the second substrate 208, or the first and second substrates 201, 208.

| Issue Addressed | Parameter | Maximize or Minimize Parameter |
| --- | --- | --- |
| Thermal Mass | $\rho c_p$ (Volumetric Heat Capacity) | Minimize |
| Thermal Gradients | k (Thermal Conductivity) | Maximize |
| Buckling/CTE | $\frac{k}{\alpha}$ (Thermal Conductivity/Coefficient of Thermal Expansion) | Maximize |
| Mechanical Stiffness | E (Young's Modulus) | Maximize |

In a representative embodiment, the second substrate 208 comprises silicon. Generally, the silicon layer that forms the second substrate 208 has a thickness of approximately 0.3 to 1.5 mm. Illustratively, the second substrate 208 comprises <1,0,0> Si having a thickness of approximately 0.675 mm. In a representative embodiment, first substrate 201 comprises, <1,0,0> Si wafer having a thickness of approximately 0.675 mm, and the second substrate 208 comprises two <1,0,0> Si wafers having a thickness of approximately 0.675 mm each. It was discovered that the use of two wafers for second substrate 208 provides somewhat improved retention time repeatability. Notably, the second substrate 208 does not require special polishing or doping. Moreover, and although not essential, the first substrate 201 may be made of the same material and to the same specifications as the second substrate 208.

It is noted that the use of silicon for the second substrate 208, or the first and second substrates 201, 208 is merely illustrative. More generally, the materials selected for the second substrate 208, or the first and second substrates 201, 208 are selected to have a volumetric heat capacity ($\rho c_p$) less than approximately $$3.0 \times 10^6 \frac{J}{m^3 K} \text{ at } 25°C.;$$

a thermal conductivity (k) greater than approximately $$100 \frac{W}{mK} \text{ at } 25°C.;$$

a ratio or thermal conductivity to coefficient of thermal expansion $$\left(\frac{k}{\alpha}\right)$$

greater than approximately $$25 \frac{W}{m\{ppm\}} \text{ at } 25°C.;$$

and a Young's Modulus (E) greater than approximately 100 GP.

These physical characteristic are desired in order to achieve faster heating and cooling of the column heating apparatus 200 within several bounds including low thermal mass, mechanical stiffness, low thermal gradients and resistance to deformation. Table 1 compares these four characteristics across a range of materials.

TABLE 1

| Parameter | Silicon | Aluminum | Aluminum Nitride | Pyrex | Diamond | Silicon Carbide | Copper | Tungsten | 85% Tungsten 15% Copper | Molybdenum |
|---|---|---|---|---|---|---|---|---|---|---|
| $\rho c_p (10^6$ J/cm$^3$K) | 1.64 | 2.43 | 2.44 | 1.67 | 1.80 | 2.05 | 3.42 | 2.58 | 2.85 | 2.55 |
| k(W/mK) | 130 | 205 | 140 | 1 | 1000 | 300 | 401 | 174 | 215 | 138 |
| $\frac{k}{\alpha}$(W/m-ppm) | 50 | 8.91 | 31.1 | 0.25 | 847 | 108 | 23.6 | 40.5 | 28.9 | 27.6 |
| E(GPa) | 130 | 69 | 308 | 64 | 1220 | 450 | 117 | 400 | 310 | 329 |

Based on the foregoing, the material selected for the second substrate 208, or the first and second substrates 201, 208 preferentially has a volumetric heat capacity less than approximately $$3.0 \times 10^6 \frac{J}{cm^3 K} \text{ at } 25°C.$$

Therefore, copper, alumina, nichrome, stainless steel, nickel, sapphire, silicon nitride, tungsten carbide, beryllium oxide, brass, bronze, aluminum brass, iron, and beryllium are not preferred materials for the second substrate 208, or the first and second substrates 201, 208.

The material selected for the second substrate 208, or the first and second substrates 201, 208 preferentially has a thermal conductivity greater than approximately $$100 \frac{W}{mK} \text{ at } 25°C.$$

Therefore, Pyrex glass, mica, titanium, quartz glass, gallium arsenide, germanium, boron nitride, zirconium oxide, boron carbide, indium phosphide, niobium, rhenium, and tantalum are generally not preferred materials for the second substrate 208, or the first and second substrates 201, 208.

The material selected for the second substrate 208, or the first and second substrates 201, 208 additionally preferentially has the ratio of thermal conductivity, k, to the coefficient of thermal expansion, α, that is greater than approximately $$25 \frac{W}{m\{ppm\}} \text{ at } 25°C. \text{ (at } 25°C).$$

Therefore, aluminum, magnesium, silver, zinc, and gold are not preferred materials for the second substrate 208, or the first and second substrates 201, 208.

The material selected for the second substrate 208, or the first and second substrates 201, 208 additionally preferentially has a Young's Modulus greater than approximately 100 GPa. Therefore, graphite is not a preferred material for the second substrate 208, or the first and second substrates 201, 208.

Based on the analysis above, illustrative materials that can be used for the second substrate 208, or the first and second substrates 201, 208 and meet all of the preferred material characteristics comprise silicon, aluminum nitride, diamond, silicon carbide, tungsten, molybdenum, alloys of tungsten (particularly with copper), alloys of molybdenum (particularly with copper), and combinations thereof.

Heater assembly 210 is disposed over the first substrate 201 and comprises a heating element 205 disposed between the first intervening layer 206 and the second intervening layer 207. The first and second intervening layers 206, 207 are generally made from the same material, and each have a second comparatively low thermal mass. Moreover, the first and second intervening layers 206, 207 are each made from a material that is electrically insulating. Notably, if the first and second substrates 201, 208 are electrically insulating, the first and second intervening layers 206, 207 can be foregone. However, if the material can become more electrically conducting at comparatively high temperatures (e.g., silicon), then electrical insulation is needed between the heating element and first and second substrates 201, 208. As such, in a representative embodiment in which first and second substrates are silicon, first and second intervening layers 206, 207 are needed. Notably, however, in another representative embodiment, rather than including first and second intervening layers 206, 207, the sides of the first and second substrates 201, 208 facing the heating element may be coated with a layer of glass or other dielectric to perform this insulating function.

The heating element 205 is illustratively a resistive heating element, such as a wire heater or a foil heater. Other types of heating elements are contemplated. As should be appreciated, the heating element is beneficially quite thin, and thereby does not substantially interfere with the desirably flat nature of each of the layers of the column heating apparatus 200. With known thin film fabrication methods, such comparatively thin heating elements that are within the purview of one of ordinary skill in the art are contemplated.

Like the comparatively low thermal masses of the first and second substrates 201, 208, the comparatively low thermal mass of the first and second intervening layers 206, 207 ensures they heat comparatively quickly and will not retain heat very well. As such, the heater assembly 210 can be heated quickly across its surface, and will not retain heat to the extent as other materials often used in heaters. Again, the former attribute ensures ultimately that the GC column disposed over upper surface 209 of the second substrate 208 is heated comparatively very quickly, which improves analysis time. The latter attribute enables the thorough dissipation of heat from the column heating apparatus 200 in a relatively quick and efficient manner enabling faster cycle times and improved retention time repeatability.

In a representative embodiment, the first and second intervening layers 206, 207 each comprise mica, which are of sheet silicate (phyllosilicate) minerals. Generally, mica materials are $X_2Y_{4-6}Z_8O_{20}(OH,F)_4$ in which X is K, Na, or Ca or less commonly Ba, Rb, or Cs; Y is Al, Mg, or Fe or less commonly Mn, Cr, Ti, Li, etc.; Z is chiefly Si or Al, but also may include $Fe^{3+}$ or Ti. The use of mica for first and second intervening layers 206, 207 is merely illustrative, and other materials having similar thermal mass, electrical conductivity, and resistance to mechanical distortion due to rapid temperature change as mica are contemplated. For example, fabrics such as fiberglass, and basalt provide the desired properties.

Generally, the mica layers that form the first and second intervening layers 206, 207 of the heater assembly 210 each have a thickness of approximately 0.3 mm. More generally, the material selected for the first and second intervening layers 206, 207 of the heater assembly 210 has an electrical resistivity of approximately $1\times10^{12}\Omega\cdot m$ to approximately $1\times10^{14}\Omega\cdot m$, or greater. Since mica has a comparatively low coefficient of thermal expansion (CTE), similar to silicon, it will not expand when heated or cooled and will not suffer from mechanical distortion, Furthermore, the mica is inherently flat and affords intimate contact between the substrate and the heating element. Other materials that could serve as an electrical insulator in place of mica are, for example, aluminum nitride, quartz, glass, silicon carbide, and the fabrics cited above. Compliant materials like the fabrics cited previously need not be as flat as they can be compressed to achieve intimate contact.

Spacer layer 202 is optionally disposed over the first substrate 201 and beneath the first intervening layer 206 of the heater assembly 210. A recess 203 is provided in the spacer layer 202, and receives a temperature sensor 204. The spacer layer 202 accommodates temperature sensor 204. Illustratively, spacer layer 202 is a compliant material, such as a glass fiber material. The spacer layer 202 beneficially maintains comparatively even pressure between the first intervening layer 206 of the heating element 205 and the first substrate 201. Notably, the inclusion of the temperature sensor 204 can compromise the even pressure in the absence of spacer layer 202. Uneven pressure between the first intervening layer 206 of the heater assembly 210 and the first substrate 201 can result in a reduction in the overall "flatness" of the column heating apparatus 200, leading to thermal gradients and "hot spots," and can thus compromise performance of the GC column.

As alluded to above, the controller 106 receives temperature data from the temperature sensor 204, and based on these data provides control signals to the power source 107. Based on the control signals from the controller 106, the power source 107 adjusts electrical power to the heater assembly 210 to maintain the temperature of the GC column at a substantially constant value or to cause it to change according to some desired and repeatable program.

Figure 2B:
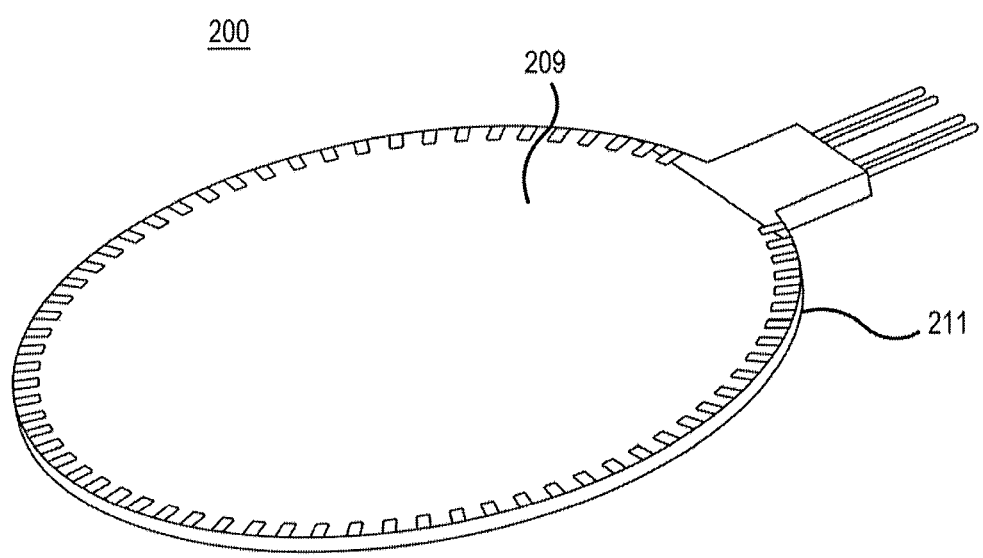
FIG. 2B shows the apparatus for heating a GC column of FIG. 2A after assembly.

FIG. 2B shows the column heating apparatus 200 of FIG. 2A for heating a GC column after assembly. The column heating apparatus 200 includes a grommet 211 that is used to secure the various layers of the column heating apparatus 200. Illustratively, the grommet 211 comprises stainless steel. Other means of securing the layers are also contemplated, such as brackets, clips etc. The requirements of the grommet or other securing means are that it can tolerate the elevated temperatures (e.g. 450° C.) and still maintain sufficient pressure on the column heating apparatus 200. High temperature metals are the preferred material.

Figure 2C:
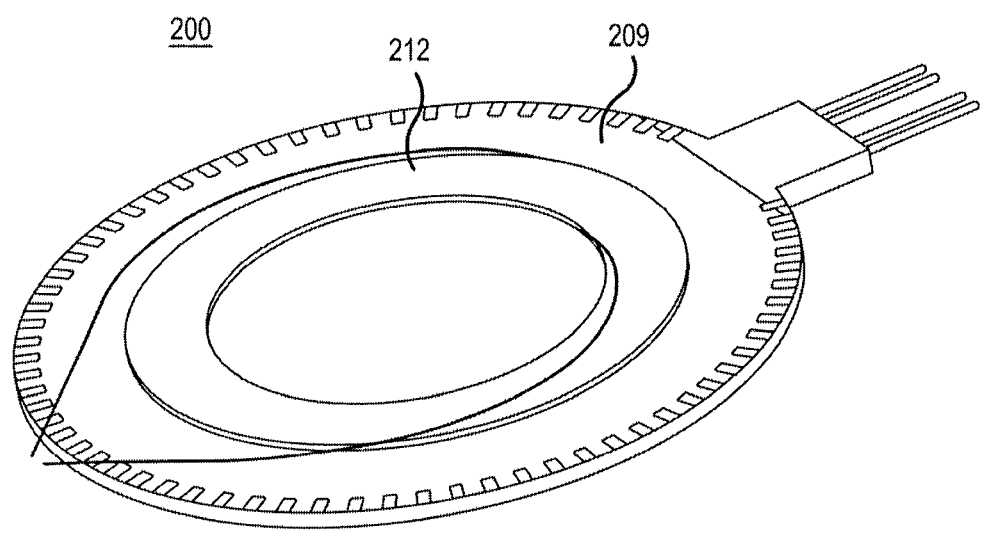
FIG. 2C shows the apparatus of FIG. 2B having the GC column disposed thereover.

FIG. 2C shows the column heating apparatus 200 of FIG. 2B having the GC column 212 disposed thereover. As shown, the GC column 212 is oriented in a comparatively flat spiral and is disposed over upper surface 209 of the column heating apparatus 200, and is in thermal contact with the upper surface 209. The GC column 212 is in thermal contact with the column heating apparatus 200 through either direct contact with the upper surface 209 or with a substantially close proximity to the upper surface 209 to transfer heat from the column heating apparatus to the GC column. In a representative embodiment, the GC column comprises a fused silica capillary column. The dimensions of the GC column 212 vary, but typical inside diameters range from approximately 100 μm to approximately 530 μm. Typical lengths range from approximately 5 meters to approximately 60 meters. The coiling of GC column 212 in representative embodiments may be a substantially planar spiral having one or more "stacked" so that the GC column 212 is in thermal contact with the column heating apparatus 210, which is substantially planar, as described above. Notably, GC column 212 can be coiled on supports having a diameter of approximately 70 mm to approximately 200 mm in a multi-layer toroid. In some embodiments, more than one GC column 212 may be disposed over the column heating apparatus 200, wherein both GC columns 212 are in thermal contact with the column heating apparatus 200.

Illustratively, GC column 212 has a length up to approximately 60 m with an inner diameter of 320 μm (or smaller internal diameter) and comprises a fused silica capillary column. Alternatively, GC column 212 can have a length less than 60 m but can have an inner diameter of 530 μm. The column may also be metal and may also be packed with stationary phase.

In operation, after the GC column 212 is provided over the upper surface 209 of the second substrate, the heating element is activated, and begins to heat the various layers of the column heating apparatus 200. Most importantly, the heater assembly 210 heats the second substrate 208, and in turn heats the GC column 212. The heating of the GC column 212 is substantially uniform and efficient due to the various characteristics of the components of the apparatus as discussed above. After a specific run is completed, the GC column 212 and the column heating apparatus 200 are cooled to reach substantially its initial temperature for the analysis. Because of the various components of the column heating apparatus 200 as discussed above, the column heating apparatus 200 cools comparatively quickly to its initial temperature, and does not substantially retain heat from the previous run. As such, when the next analysis is started, the column heating apparatus 200 and the GC column 212 are at substantially the same initial temperature from the previous run. Moreover, the cycle time is comparatively improved over other known heating arrangements used in GC systems.

Figure 2D:
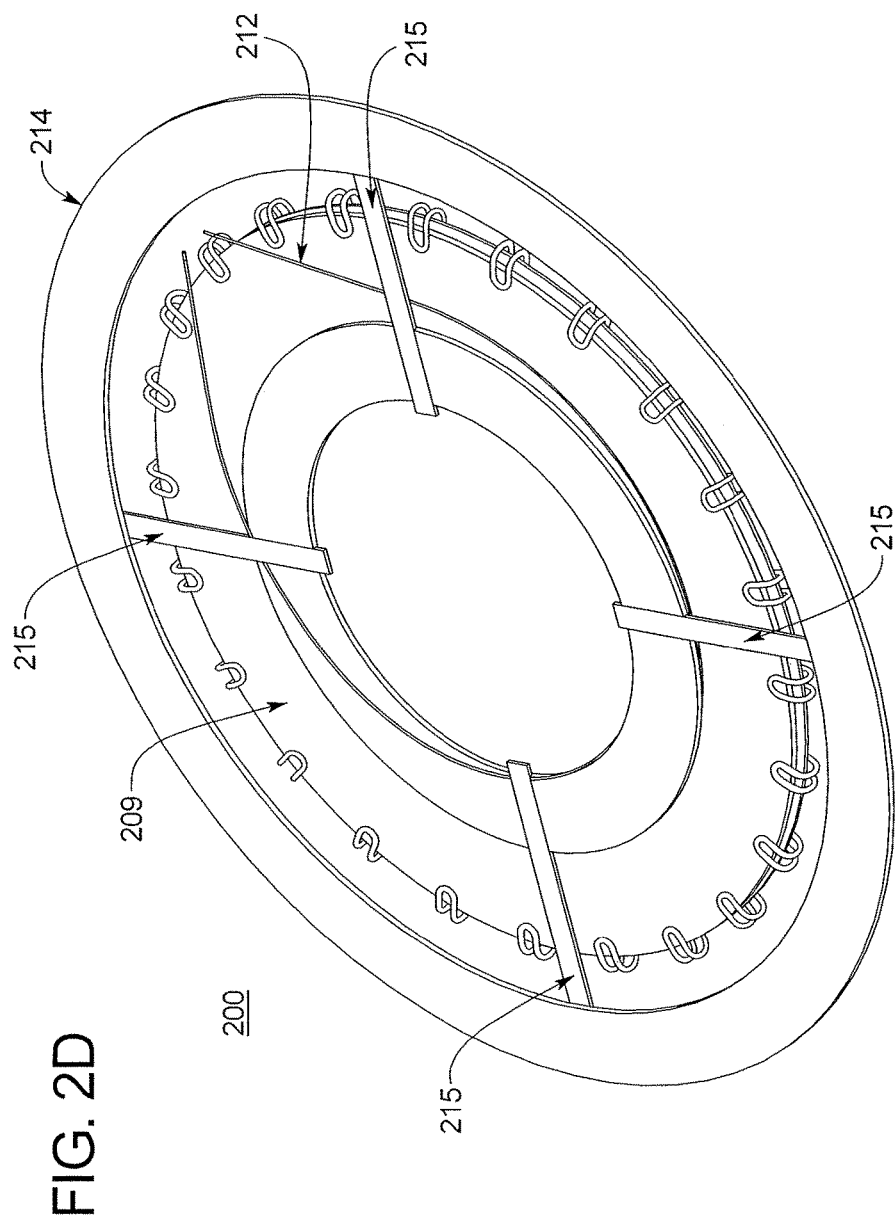
FIG. 2D shows the column heating apparatus of FIG. 2B having the GC column disposed thereover in accordance with another representative embodiment.

FIG. 2D shows the column heating apparatus 200 of FIG. 2B having the GC column 212 disposed thereover in accordance with another representative embodiment. As can be appreciated, the column heating apparatus 200 of FIG. 2D shares certain aspects, details and features common to those of column heating apparatus 200 described in connection with FIG. 2C above. Often, such common aspects, features and details are not repeated. As noted above, the GC column 212 is oriented in a comparatively flat spiral and is disposed over upper surface 209 of the column heating apparatus 200, and makes thermal contact with the upper surface 209 through the portion that is in direct or close physical contact with the upper surface 209. Again, the coiling of GC column 212 in representative embodiments may be a substantially planar spiral having one or more "stacked" so that the GC column 212 is in thermal contact with the column heating assembly 210, which is substantially planar, as described above. Persons skilled in the art would appreciate how a GC column 212 may be "stacked" or "wound" to achieve the desired objectives described herein. In accordance with the depicted representative embodiment, the GC column 212 is held in place over the upper surface 209 by GC column supports 215 mounted to GC column bracket 214. Illustratively, the GC column supports 215 can be constructed of thin strips of metal such as aluminum, nickel, or stainless steel. More generally, the GC column supports 215 may be made of a material that is able to support the GC column 212 on the upper surface 209 and tolerate the temperature exposure (up to 450° C.). The GC column bracket 214 serves as a structural element for GC column 212 and ensures repeatable positioning of the GC column 212 on upper surface 209 for reproducible chromatographic performance. The GC column bracket 214 can be mounted in the GC system using one or more of a variety of known elements including, but not limited to, screws, clamps, and magnets (not shown).

Figure 2E:
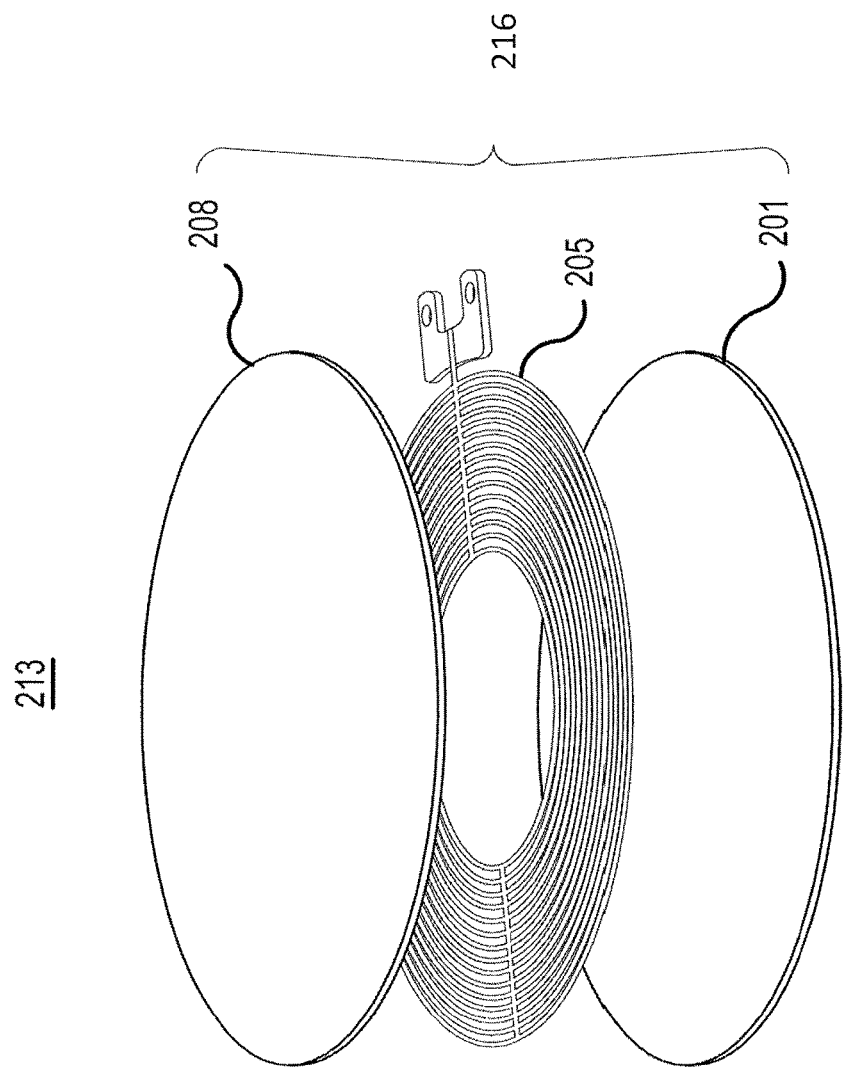
FIG. 2E shows an exploded view of an apparatus for heating a GC column in accordance with a representative embodiment.

FIG. 2E shows an exploded view of a GC column heating apparatus 213 (sometimes referred to as "an apparatus") in accordance with a representative embodiment. Many aspects of the column heating apparatus 213 are substantially identical to those of column heating apparatus 200 described above. As such, many details of various features that are common to those of column heating apparatus 200 are not repeated. Notably, the various characteristics of the common elements of the column heating apparatuses 200, 213 are the same. In embodiments where the spacer layer 202 is omitted, the temperature sensor may be disposed within a substrate 208, 201. In embodiments where the intervening layers 206, 207 are omitted, the temperature sensor may be disposed within a substrate layer 208, 201 or within the spacer layer 202, which may be located below the first substrate 201 (i.e., further away from the heating element 205 than the first substrate 201).

The column heating apparatus 213 comprises the first substrate 201 having heating element 205 disposed thereover.

A heater assembly 216 comprises heating element 205. Notably, therefore, the heater assembly 216 does not comprise first and second intervening layers 206, 207, which were noted above as being optional. However, the heating element 205 is contemplated for use in the column heating apparatuses 200, 213 of the representative embodiments described in connection with FIGS. 2A-2D.

The heating element 205 is illustratively a resistive heating element, such as a wire heater or a foil heater. Other types of heating elements are contemplated. As should be appreciated, the heating element 205 is beneficially quite thin, and thereby does not substantially interfere with the desirably flat nature of each of the layers of the column heating apparatus 213. The heating element 205 may be of any substantially planar shape, including non-uniform shapes. With known thin film fabrication methods, such comparatively thin heating elements that are within the purview of one of ordinary skill in the art are contemplated.

The column heating apparatus 213 also comprises second substrate 208 disposed over the heating element 205. The second substrate 208 is configured to be in thermal contact with the GC column 212 (not shown in FIG. 2D), which may comprise direct contact with the upper surface 209 or with a substantially close proximity to the upper surface 209 to transfer heat from the column heating apparatus to the GC column 212. In embodiments, the GC column 212 may be in thermal contact with the second substrate 208 despite an intervening layer (not shown) between the GC column 212 and the second substrate 208. Illustratively, the GC column is disposed over an upper surface 209 of the second substrate 208, and heat from heating element 205 is transferred through the second substrate 208 as described above in connection with the representative embodiments of FIGS. 2A-2D. The first and second substrates 201, 208 may comprise single layer or multiple layers of the same or different materials. Through the heat distribution of the second substrate 208 described above, the apparatus 213 substantially uniformly heats the GC column contacting the second substrate 208.

Figure 3:
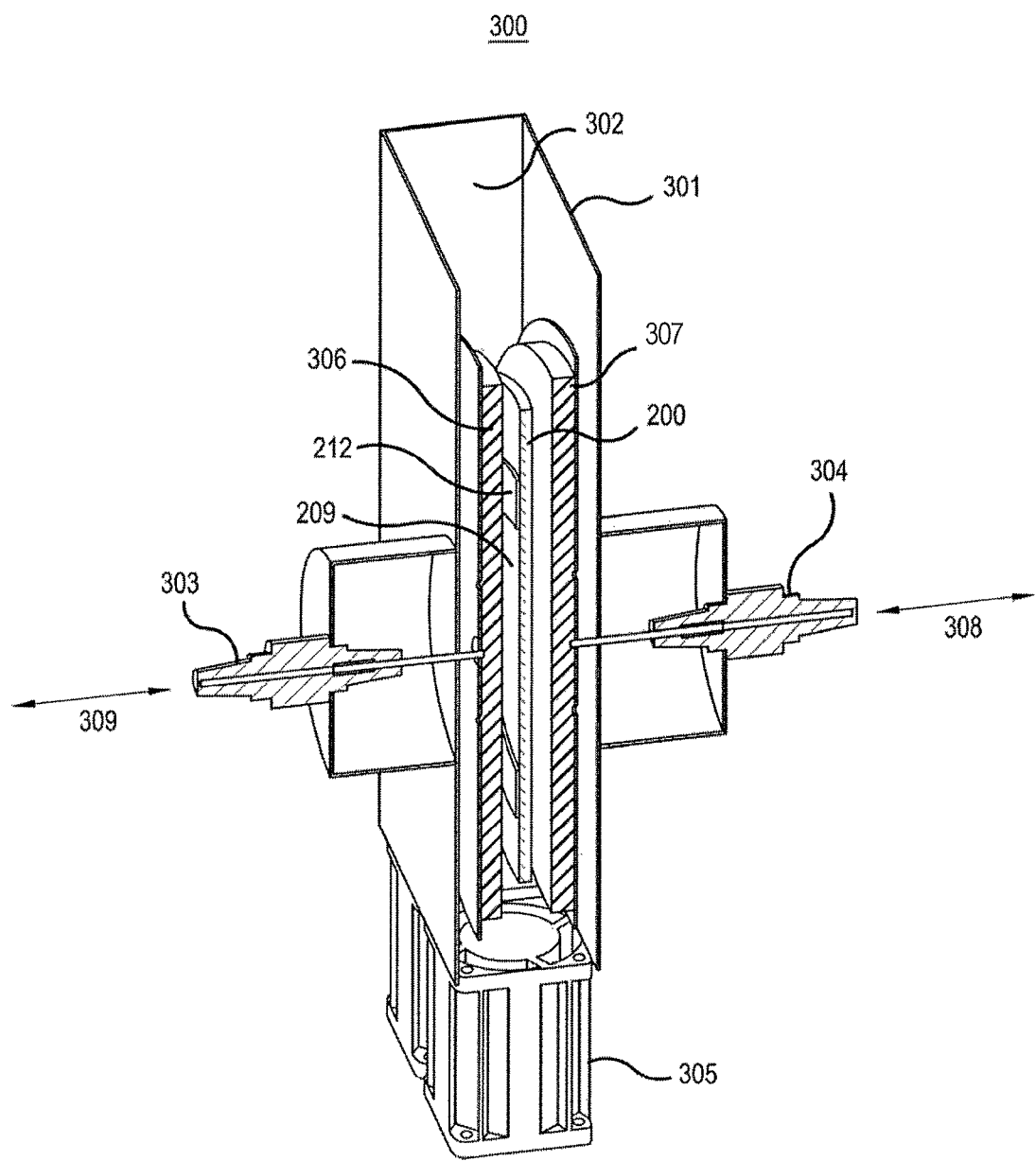
FIG. 3 shows an isometric partial cutaway view of an apparatus for heating and cooling a GC column in accordance with a representative embodiment.

FIG. 3 shows an isometric partial cutaway view of a column temperature control apparatus 300 (sometimes referred to as "an apparatus") for heating and cooling a GC column 212 in accordance with a representative embodiment. Many aspects of the column temperature control apparatus 300 are substantively the same as those described above in connection with the representative embodiments of FIGS. 1-2E, and will not be repeated in order to avoid obscuring the description of the column heating and cooling apparatus 300.

The column temperature control apparatus 300 comprises a housing 301, which has an interior portion 302. The housing 301 is configured to hold column heating apparatus 200, or the column heating apparatus 213 in its interior portion. Generally, the housing 301 can be made of one or more of a number of materials that are compatible with the thermal requirements of the column heating and cooling apparatus 300. For example, the housing 301 comprises a metal or metal alloy, or thermally suitable polymeric materials. Notably, as described more fully below, a first actuator 303 and a second actuator 304 are configured to move a first thermal insulation layer 306 and a second thermal insulation layer 307 to be in contact with and out of contact with the outer sides of the column heating apparatus 200 and the GC column 212. These thermal insulation layers at least have the ability to insulate the column and column heater from heat loss, but may also have additional insulative properties as would be appreciated by those skilled in the art. Illustratively, the outer sides of the column heating apparatus 200 include the upper surface 209 of the second substrate 208, and the lower surface (i.e., the surface opposing the upper surface 209) of the first substrate 201.

As described more frilly below, the first actuator 303 (as indicated by arrows 309) and the second actuator 304 (as indicated by arrows 308) are each configured to move inwardly before a heating cycle begins in order to maintain the first and second thermal insulation layers 306, 307 in comparatively firm contact with the outer surfaces of the column heating apparatus 200 and the GC column 212; and are configured to move outwardly (again, as indicated by arrows 308, 309) after a heating cycle ends and before a cooling cycle begins in order to separate the first and second thermal insulation layers 306, 307 from the outer surfaces of the column heating apparatus 200 and the GC column 212. Notably, in FIG. 3, the first actuator 303 and the second actuator 304 shown in their inward-most position and thereby the first and second thermal insulation layers 306, 307 are in comparatively firm contact with the outer surfaces of the column heating apparatus 200. As such, in FIG. 3 the various components of column heating and cooling apparatus 300 are positioned for a heating cycle.

The column heating and cooling apparatus 300 also comprises a fan 305 situated to provide airflow in the interior portion 302 during a cooling cycle. The fan 305 may comprise a single fan or multiple fans to direct airflow in the interior portion. Note that while the fan or fans are configured to blow air over the column heating apparatus 200, they could also be configured to pull air over the column heating apparatus 200. Notably, the fan 305 may be oriented in a manner perpendicular to the orientation depicted in FIG. 3 and this can direct flow perpendicular to the direction of flow of FIG. 3.

The first and second thermal insulation layers 306, 307 are made of a material suitable to provide ample thermal insulation without interfering with the performance of the GC system. Illustratively, the first and second thermal insulation layers 306, 307 are made of a glass fabric material having a thickness of approximately 0.25 in., and can be provided as "blankets" to improve conformance of the first and second thermal insulation layers 306, 307 to the outer surfaces of the column heating apparatus 200 with which they contact. Alternatively, the first and second thermal insulation layers 306, 307 may comprise other types of insulation including, but not limited to fiberglass, glass cloth, basalt, and the like. The material selected for the first and second thermal insulation layers 306, 307 generally needs to provide a sufficient thermal barrier between the column heating apparatus 200 and the ambient environment during a GC run, while being capable of being cooled comparatively thoroughly and quickly after the GC run.

As noted above and as described more fully below, the first and second actuators 303, 304 are configured to engage the first and second thermal insulation layers 306, 307 to be in comparatively good thermal contact with the outer surfaces of the column heating apparatus 200 during a heating cycle, and to create a space of separation between the first and second thermal insulation layers 306, 307 and the column and outer surfaces of the column heating apparatus 200 during a cooling sequence. The first and second actuators 303, 304 may be one of a number of known mechanical actuators that are configured to move the first and second thermal insulation layers 306, 307. The movement of the first and second actuators 303, 304 to engage and separate the first and second thermal insulation layers 306, 307, may be mechanical, pneumatic, magnetic, manual, or may be through electrical control. Moreover, while two actuators are shown, it is noted that more or fewer actuators are contemplated by the present teachings to effect the movement of the first and second thermal insulation layers 306, 307 through direct or indirect motion system (e.g., a cable and pulley system).

Figure 4A:
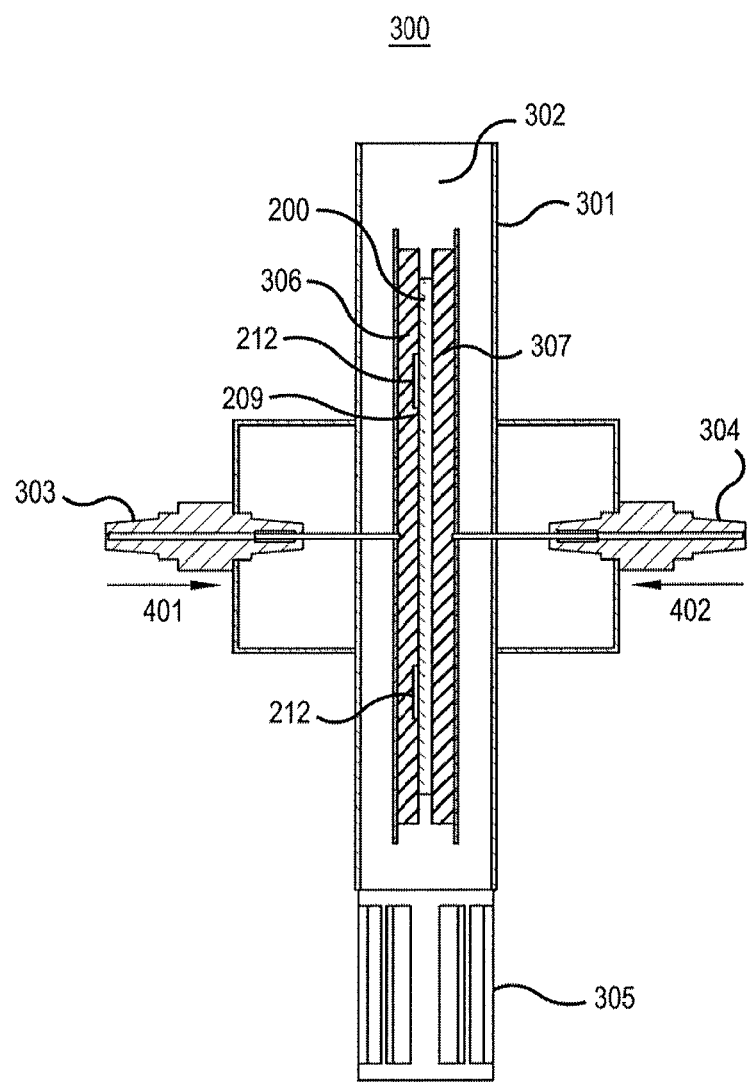
FIG. 4A shows a cross-sectional view of an apparatus for heating and cooling a GC column in accordance with a representative embodiment.

FIG. 4A shows a cross-sectional view of the column heating and cooling apparatus 300 in accordance with a representative embodiment. Again, many aspects of the column heating and cooling apparatus 300 are substantively the same as those described above in connection with the representative embodiments of FIGS. 1-3, and will not be repeated in order to avoid obscuring the description of the column heating and cooling apparatus 300.

In FIG. 4A the first actuator 303 and the second actuator 304 are shown in their inward-most position (as indicated by arrows 401, 402, respectively), and thereby, the first and second thermal insulation layers 306, 307 are in comparatively firm contact with the outer surfaces of the column heating apparatus 200. As such, in FIG. 4A the various components of column heating and cooling apparatus 300 are positioned for a heating cycle. As described below, the pressure of the first and second thermal insulation layers 306, 307 ensures good thermal contact between the GC column 212 and the outer surfaces of column heating apparatus 200, which aids to improve retention time repeatability, cycle time, and energy efficiency.

The engagement of the first and second thermal insulation layers 306, 307 with the outer surfaces of the column heating apparatus 200 usefully improves thermal efficiency by reducing the loss of thermal energy to the ambient environment. The first thermal insulation layer 306 also provides protection of the GC column 212 from the ambient environment. Notably, the first thermal insulation layer 306 provides a thermal break from the ambient environment and thus reduces the susceptibility of the GC column to the temperature of the ambient environment, which can be an uncontrolled environment. Similarly, although less directly, the second thermal insulation layer 307 also provides protection of the GC column 212 from the ambient environment by providing substantial thermal isolation of the first substrate 201 (not shown in FIG. 4A) from the ambient environment.

As such, the engagement of the first and second thermal insulation layers 306, 307 results in faster heating of the GC column 212, and the use of less energy to reach a certain temperature compared to certain known GC column heaters. The first and second actuators 303 and 304 are configured to be set in positions to be fully engaged (i.e., so that the first and second thermal insulation layers 306, 307 are in contact with the GC column 212 and column heating apparatus 200) or fully disengaged (i.e., so that the first and second thermal insulation layers 306, 307 are not in contact with the GC column 212 and column heating apparatus 200). In addition, the first and second actuators 303 and 304 can be asymmetrically positioned. For example, first actuator 303 may be moved away from column heating apparatus 200 while second actuator 304 is fully engaged with column heating apparatus 200. For GC applications where the heater assembly 210 (not shown in FIG. 4A) of column heating apparatus 200 is operated near ambient temperature or at isothermal temperatures, temperature control can be improved by having a cooling flow over column heating apparatus 200 or over first and second thermal insulation layers 306, 307 in contact with column heating apparatus 200 and GC column 212. To achieve this, either or both of the first and second thermal insulation layers 306, 307 can be moved a small distance apart from GC column 212 and column heating apparatus 200 or left in contact with them. The fan 305 can be turned at maximum power, run under proportional power control, or turned off to allow variable amounts of cooling air to move across the GC column 212 and column heating apparatus 200.

Finally, it is noted that the first and second thermal insulation layers 306, 307 may be foregone, and the column heating and cooling apparatus 300 may function in a heating cycle without them, while using the fan 305 during the cooling cycle as described below. This representative embodiment, although possible, is less beneficial than the representative embodiments comprising the first and second thermal insulation layers 306, 307 configured to engage the column heating apparatus 200 during a heating cycle as described above. Most notably, in such an embodiment where the first and second thermal insulation layers 306, 307 are foregone, the rate of heating of the GC column 212 is adversely impacted, and the general repeatability of the GC column 212 suffers as the GC column 212 and the column heating apparatus 200 are more susceptible to changes in the ambient environment.

Figure 4B:
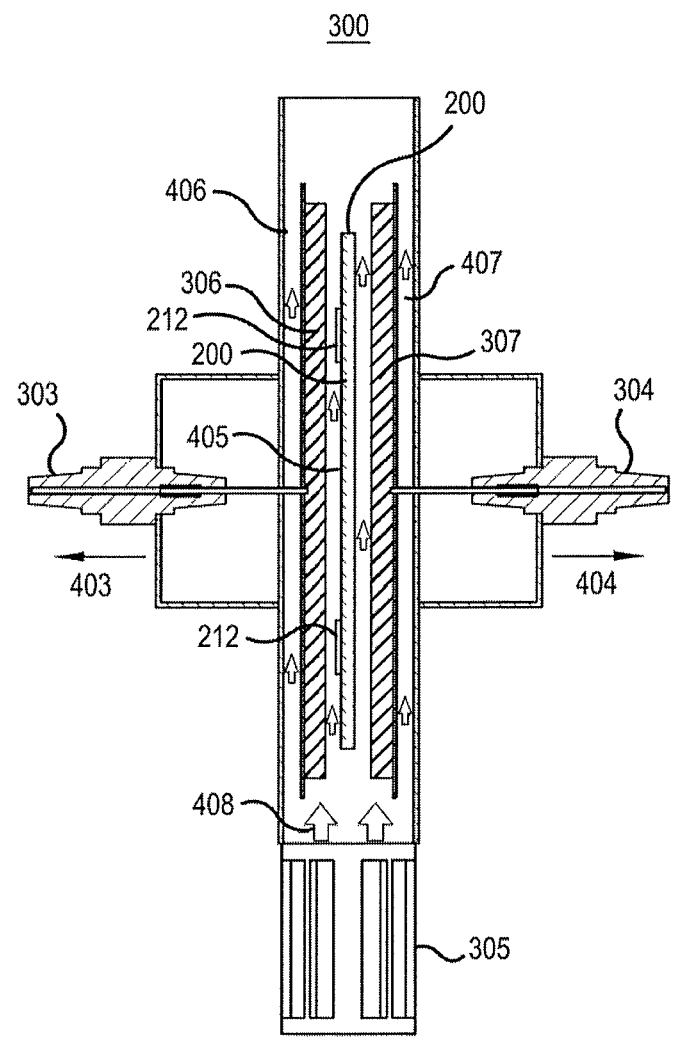
FIG. 4B shows a cross-sectional view of an apparatus for heating and cooling a GC column in accordance with a representative embodiment.

FIG. 4B shows a cross-sectional view of the column heating and cooling apparatus 300 in accordance with a representative embodiment. Again, many aspects of the column heating and cooling apparatus 300 are substantively the same as those described above in connection with the representative embodiments of FIGS. 1-4A, and will not be repeated in order to avoid obscuring the description of the column heating and cooling apparatus 300.

In FIG. 4B the first actuator 303 and the second actuator 304 are shown in their outward-most positions (as indicated by arrows 403, 404, respectively), and thereby, the first and second thermal insulation layers 306, 307 are separated from the outer surfaces of the column heating apparatus 200. As such, in FIG. 4B the various components of column heating and cooling apparatus 300 are positioned for a cooling cycle. As described below, the removal of the first and second thermal insulation layers 306, 307 from contact with the column heating apparatus 200 improves the efficiency of cooling during the cooling cycle, increasing both the rate and completeness of the cooling. Beneficially, not only is the cooling rate increased, which results in an improvement in the cycle time, but also the removal of latent heat is improved enabling a Comparatively high repeatability of the retention time of a particular analyte.

With the separation of the first and second thermal insulation layers 306, 307 from the outer surfaces of column heating apparatus 200, a plurality of channels 405 are created between the inner surfaces of the first and second thermal insulation layers 306, 307 and the column heating apparatus 200. First and second outer channels 406, 407 respectively exist in the housing on the outer surfaces of the first and second thermal insulation layers 306, 307. During operation, the fan 305 is engaged and air (indicated by arrows 408) from the fan flows in the channels 405, and the first and second outer channels 406,407, to remove thermal energy by forced convection from the region surrounding the column heating apparatus 200. By separating the first and second thermal insulation layers 306, 307 from the column heating apparatus 200 as shown in FIG. 4B, the air flows over not only the outer surfaces of the column heating apparatus 200, but also over both sides of each of the first and second thermal insulation layers 306, 307 efficiently removing residual heat that could otherwise be trapped in the column heating and cooling apparatus 300. For example, if the first and second thermal insulation layers 306, 307 remained in their engaged position in contact with the outer surfaces of column heating apparatus 200 (e.g., as shown in FIGS. 3 and 4A) the air flow during a cooling cycle would only flow over the outer portions of the first and second thermal insulation layers 306, 307 (i.e., only in the first and second outer channels 406,407), and not through inner channel 405. As such, the air would not flow over the outer surfaces of column heating apparatus 200 or over the inner surfaces of the first and second layers of insulation 306, 307. While cooling would be improved over many known GC heater devices, the likelihood of residual heat in regions not flushed with air flow from the fan 305 would be increased (i.e., as depicted in FIG. 4A) compared to the representative embodiment in which the first and second thermal insulation layers 306, 307 are separated from contact with the outer surfaces of column heating apparatus 200. This residual heat would increase the cycle time, and if removed insufficiently could decrease the repeatability of the retention time of a particular analyte. In addition, the first and second thermal insulation layers 306, 307 could be moved until they contact the housing 301, increasing the space between column heating apparatus 200 and first and second thermal insulation layers 306,307. While cooling would be improved over many known GC heater devices, the likelihood of residual heat in regions not flushed with air flow from the fan 305 would be increased compared to that attained via the representative embodiment in which the first and second thermal insulation layers 306, 307 are separated from contact with the outer surfaces of column heating apparatus 200 (i.e., as depicted in FIG. 4B). This residual heat would increase the cycle time, and if removed insufficiently could deleteriously decrease the repeatability of the retention time of a particular analyte. An additional construct is to move only one of the insulation pads away from column heating apparatus 200. Air flow across the exposed side of column heating apparatus 200 (likely first substrate 201) would permit cooling without exposing the GC column 212 interfaced with second substrate 208 to cooling air flow. Such a configuration may allow improved retention time stability at near ambient temperatures.

In view of this disclosure it is noted that the methods and devices can be implemented in keeping with the present teachings. Further, the various components, materials, structures and parameters are included by way of illustration and example only and not in any limiting sense. In view of this disclosure, the present teachings can be implemented in other applications and components, materials, structures and equipment needed to implement these applications can be determined, while remaining within the scope of the appended claims.

The invention claimed is:

1. An apparatus, comprising:
a first substrate;
a heating element disposed adjacent to the first substrate; and
a second substrate comprising silicon, the second substrate being disposed adjacent to the heating element, the second substrate having a first side and a second side, wherein the second substrate is capable of transferring heat from the heating element to a gas chromatography column that is in thermal contact with the second substrate;
wherein the heating element is disposed between the first substrate and the second substrate.

2. An apparatus as claimed in claim 1, further comprising a heater assembly, comprising: the heating element disposed between a first intervening layer and a second intervening layer.

3. An apparatus as claimed in claim 2, wherein the heater assembly is electrically insulated from the substrates.

4. An apparatus as claimed in claim 1, wherein the heating element comprises a foil heater or a wire heater.

5. An apparatus as claimed in claim 1, wherein the first substrate comprises crystalline silicon.

6. An apparatus as claimed in claim 5, wherein the crystalline silicon comprises polycrystalline silicon.

7. An apparatus as claimed in claim 1, wherein the second substrate comprises crystalline silicon.

8. An apparatus, comprising:
a first substrate;
a heating element adjacent to the first substrate; and
a second substrate, the second substrate being adjacent to the heating element, the second substrate comprises the following attributes: a volumetric heat capacity less than 3.0×

$$10^6 \frac{J}{m^3 K} \text{ at } 25°C;$$

a thermal conductivity greater than $$100 \frac{W}{mK} \text{ at } 25°C;$$

a ratio of thermal conductivity to coefficient of thermal expansion greater than approximately $$25 \times 10^6 \frac{W}{m} \text{ at } 25°C;$$

and a mechanical stiffness greater than 100 GPa, wherein the second substrate is capable of transferring heat from the heating element to a gas chromatography column that is in thermal contact with the second substrate.

9. An apparatus as claimed in claim 8, further comprising a heater assembly, comprising: the heating element disposed between a first layer and a second intervening layer.

10. An apparatus as claimed in claim 8, wherein the second substrate comprises aluminum nitride, diamond, silicon carbide, tungsten, molybdenum, an alloy of tungsten, an alloy of molybdenum, or combination thereof.

11. An apparatus as claimed in claim 8, wherein the heating element comprises a foil heater or a wire heater.

12. An apparatus, comprising:
   a housing configured to receive a column heating apparatus, the column heating apparatus comprising a first side and a second side;
   a first thermal insulation layer adjacent to the first side;
   a second thermal insulation layer adjacent to the second side;
   a heater assembly disposed within the first side and the second side; and
   an actuator connected to the housing and configured to move the first and second thermal insulation layers in contact with the first and second sides, respectively, during a heating sequence, and to move the first and second thermal insulation layers out of contact with the first and second sides, respectively, during a cooling sequence.

13. An apparatus as claimed in claim 12, wherein during the cooling sequence, channels formed between the thermal insulation layers and the housing and between the heater assembly and interior wall of the insulation layers are configured to allow cooling fluid to pass through and reduce the temperature of the column heating apparatus.

14. An apparatus as claimed in claim 12, further comprising one or more fans connected to the housing, wherein the one or more fans are configured to force the cooling fluid through the first channels.

15. An apparatus as claimed in claim 12, wherein the column heating apparatus comprises:
   a first substrate;
   a heater assembly adjacent to the first substrate;
   a second substrate adjacent to the heater assembly, the second substrate having a first side and a second side, the second side configured to have the gas chromatography column in thermal contact therewith, wherein heat from the heater assembly is transferred through the second substrate and substantially uniformly heats the gas chromatography column contacting the second substrate.

16. An apparatus as claimed in claim 15, further comprising a heater assembly, comprising: the heating element disposed between a first intervening layer and a second intervening layer.

17. An apparatus as claimed in claim 16, wherein the heater assembly is electrically insulated from the substrates.

18. An apparatus as claimed in claim 17, wherein the heating element comprises a foil heater or a wire heater.

19. An apparatus as claimed in claim 15, wherein the second substrate comprises crystalline silicon.

20. An apparatus as claimed in claim 15, wherein the second substrate comprises the following attributes: a volumetric heat capacity less than $$3.0 \times 10^6 \frac{J}{m^3 K} \text{ at } 25°C;$$

a thermal conductivity greater than $$100 \frac{W}{mK} \text{ at } 25°C;$$

a ratio of thermal conductivity to the coefficient of thermal expansion greater than $$25 \times 10^6 \frac{W}{m} \text{ at } 25°C;$$

and a mechanical stiffness greater than 100 GPa.

21. An apparatus as claimed in claim 15, the second substrate comprises: aluminum nitride, diamond, silicon carbide, tungsten, molybdenum, an alloy of tungsten, an alloy of molybdenum, or combination thereof.

* * * * *

UNITED STATES PATENT AND TRADEMARK OFFICE
CERTIFICATE OF CORRECTION

| | | |
|---|---|---|
| PATENT NO. | : 10,067,101 B2 | Page 1 of 1 |
| APPLICATION NO. | : 14/802864 | |
| DATED | : September 4, 2018 | |
| INVENTOR(S) | : Sammye Elizabeth Traudt et al. | |

It is certified that error appears in the above-identified patent and that said Letters Patent is hereby corrected as shown below:

In the Specification

In Column 5, Line 6, delete "that that" and insert -- that --, therefor.

In Column 8, Line 49, delete "or" and insert -- of --, therefor.

In Column 8, Line 64, delete "GP." and insert -- GPa. --, therefor.

In Column 17, Line 26, delete "Comparatively" and insert -- comparatively --, therefor.

Signed and Sealed this
Tenth Day of September, 2019

Andrei Iancu
*Director of the United States Patent and Trademark Office*